(12) United States Patent
Pettus, IV et al.

(10) Patent No.: US 10,806,583 B2
(45) Date of Patent: Oct. 20, 2020

(54) PENILE PROSTHESIS IMPLANTATION APPARATUS AND RELATED METHODS

(71) Applicants: Joseph Atkins Pettus, IV, Madison, AL (US); Katherine Ann Byrne, Madison, AL (US); Tristan Reilly Pettus, Madison, AL (US); Rylan Connor Pettus, Madison, AL (US)

(72) Inventors: Joseph Atkins Pettus, IV, Madison, AL (US); Katherine Ann Byrne, Madison, AL (US); Tristan Reilly Pettus, Madison, AL (US); Rylan Connor Pettus, Madison, AL (US)

( * ) Notice: Subject to any disclaimer, the term of this patent is extended or adjusted under 35 U.S.C. 154(b) by 49 days.

(21) Appl. No.: 16/178,427

(22) Filed: Nov. 1, 2018

(65) Prior Publication Data

US 2020/0138579 A1    May 7, 2020

(51) Int. Cl.
   *A61F 2/26* (2006.01)
(52) U.S. Cl.
   CPC ..................................... *A61F 2/26* (2013.01)

(58) Field of Classification Search
   CPC .......................................................... A61F 2/26
   USPC ..................................................... 600/38–41
   See application file for complete search history.

(56) References Cited

U.S. PATENT DOCUMENTS

| | | | | |
|---|---|---|---|---|
| 4,244,370 A * | 1/1981 | Furlow | | A61F 2/26 606/148 |
| 7,066,878 B2 * | 6/2006 | Eid | | A61F 2/26 600/40 |
| 9,480,566 B2 * | 11/2016 | Poucher | | A61F 5/41 |
| 9,642,707 B2 * | 5/2017 | Daniel | | A61B 17/3468 |
| 2011/0054250 A1 * | 3/2011 | Morningstar | | A61F 2/26 600/40 |
| 2011/0144428 A1 * | 6/2011 | Morningstar | | A61M 25/0043 600/40 |

* cited by examiner

*Primary Examiner* — John P Lacyk
(74) *Attorney, Agent, or Firm* — Cygnet IP Law, P.A.; Stephen W. Aycock, II (57) ABSTRACT

A penile prosthesis implantation apparatus and related methods are described.

20 Claims, 6 Drawing Sheets

PENILE PROSTHESIS IMPLANTATION APPARATUS AND RELATED METHODS

FIELD

Some implementations relate generally to apparatus and related methods for implanting penile prosthesis devices and related components, and more particularly, to an instrument for penile prosthesis implantation and methods related thereto.

BACKGROUND

The penis is anatomically composed of three gross longitudinal structures: the right and left corpora cavernosa and the urethra. These three structures terminate at the glans penis. The corpora cavernosa are structures that are composed of spongy tissue and surrounded by fascia called tunica albuginea. The urethra is the conduit for urine and semen. The left and right corpora cavernosa lay dorsal to the urethra and extend from the glans penis distally to the ischial tuberosity of the pelvis proximally. During a normal erection, the deep penile artery, which runs through the corpora cavernosa, dilates and engorges the spongy tissue with blood. Engorgement of the corpora cavernosa impedes venous outflow resulting in an erection. Many disease processes can impact this normal physiology leading to erectile dysfunction or impotency.

After behavioral and medical therapies fail to correct or improve erectile dysfunction, surgery may be considered. Common devices for correcting or improving erectile dysfunction through surgery include an inflatable penile prosthesis (IPP) and a malleable prosthesis (MP). In each case, the spongy tissue of the corpora cavernosa is replaced with a device that either inflates to become rigid (in the case of IPP devices) or is always in the rigid state (in case of MP devices).

An IPP device usually comprises four components: two balloon cylinders, a pump mechanism, and a reservoir. The cylinders are implanted into the corpora cavernosa and the pump is placed in an accessible portion of the scrotum. The reservoir is typically implanted next to the bladder in the space of Retzius or else beneath the rectus muscle of the body wall. The components are connected via tubing and the reservoir is filled with saline. The device operates by filling the cylinders with saline from the reservoir when a user squeezes the pump manually. Once erection is no longer desired, the user presses a valve on the pump causing the saline to move back to the reservoir until the pump is activated again.

An MP device usually comprises two semi-rigid rods. Once implanted, the penis can be manually directed for sexual activity. These devices are typically implanted in individuals with poor manual dexterity or as temporary devices after removal of an IPP device due to infection. As the MP device is always in erection mode, it may not be the first choice for most patients.

Complications with penile prosthetics fall into two broad categories: intraoperative and long term. Intraoperatively, any violation of the urethra contaminates the operative field and the operation must be terminated. Urethral violation is the most common intraoperative complication and requires reoperation at least six weeks later for another attempt at implementing the device. Urethral violation occurs when a corporal dilator, a cylinder, or a rod crosses from the corpora cavernosum into the urethra. Other intraoperative complications can include scrotal hematoma from placement of the pump or oozing from the corporotomies, and bladder or vascular injury during placement of the reservoir. Long term complications are typically device failure, device erosion into the urethra, and infection, all of which require explantation of the prosthesis device.

As discussed above, some of the existing apparatus for implanting penile prostheses could lead to intraoperative and long-term complications. Commonly used apparatus for implanting penile prostheses, such as inflatable penile prosthesis and malleable prosthesis implantation methods, could also be susceptible to interoperative complications. It may thus be desirable to provide new and improved penile prosthesis implantation apparatus and related methods for reducing risk of intraoperative complications. Some implementations were conceived in light of the above-mentioned limitations, needs, or problems, among other things.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Some implementations can include a penile prosthesis implantation device comprising a rod having a protrusion disposed on a first side of the rod at a distance proximal to a distal end of the rod, and a channel inside the rod accessed by a fluted entry at a proximal end of the rod, the channel extending diagonally though the rod and exiting at a channel opening at the distal end of the rod. The device can also include a slot formed at the distal end of the rod and opening into the channel opening at a distal end of the slot, wherein the bottom of the slot opens into the channel, and an offset handle extending from the proximal end of the rod on a second side of the rod. The device can further include a needle pusher having a flat syringe-style plunger at a proximate end.

In some implementations, the slot can be configured to accept loading of one or more of a Keith needle or a prosthesis suture. In some implementations, the channel can extend diagonally through the rod from the first side of the rod proximally to the second side of the rod opposite the first side distally.

In some implementations, the needle pusher can be operable to push a Keith needle out of the distal end of the rod. In some implementations, the flat syringe-style plunger can be operable to push a Keith needle through the channel. In some implementations, the penile prosthesis implantation device can be operable to dilate corpora cavernosum.

In some implementations, the penile prosthesis implantation device can be operable to measure a proximal length of a corpora cavernosum. In some implementations, the penile prosthesis implantation device can be operable to distally measure a corpora cavernosum.

Some implementations can include a method for implanting a penile prosthesis. The method can include opening corpora cavernosum via corporotomy, selecting the penile prosthesis, and threading sutures of the penile prosthesis through a Keith needle. The method can also include loading the Keith needle into a distal tip of a penile prosthesis implantation device, bringing out the sutures through a distal slot of the penile prosthesis implantation device, and holding the sutures in place against an offset handle of the penile prosthesis implantation device.

The method can further include preventing the Keith needle from protruding from the distal tip of the penile prosthesis implantation device, and advancing the penile prosthesis implantation device distally through a corpora cavernosum with the offset handle directed laterally away from a penis. The method can also include advancing a needle pusher through a fluted entrance of the penile prosthesis implantation device, once the penile prosthesis implantation device is in place, causing the Keith needle to pierce and exit from the glans penis.

In some implementations, the Keith needle exits the glans penis at an angle which situates the exit of the Keith needle away from the urethra. In some implementations, the distal tip has a slit to facilitate loading of the Keith needle. In some implementations, the distal tip has a slit to facilitate loading of a prosthesis suture.

In some implementations, the sutures are passed through a channel of the penile prosthesis implantation device. In some implementations, the channel extends diagonally through the penile prosthesis implantation device from a first side of the penile prosthesis implantation device proximally to a second side of the penile prosthesis implantation device opposite the first side distally.

In some implementations, the needle pusher pushes the Keith needle out of the distal tip of the penile prosthesis implantation device. In some implementations, the handle extends from a proximal end of the penile prosthesis implantation device. In some implementations, a flat syringe-style plunger is placed on one end of the needle pusher to push the Keith needle through the penile prosthesis implantation device.

Some implementations can include a method for measuring length of corpora cavernosum. The method can include opening the corpora cavernosum via corporotomy, and advancing a penile prosthesis implantation device distally through the corpora cavernosum to measure a distal corporal length, wherein an offset handle of the penile prosthesis implantation device is directed laterally away from a penis. The method can also include withdrawing the penile prosthesis implantation device from the corpora cavernosum, and advancing the penile prosthesis implantation device proximally through the corpora cavernosum to measure a proximal corporal length of the corpora cavernosum. The corporal length is the proximal length plus distal length.

In some implementations, the offset handle extends from a proximal end of the penile prosthesis implantation device. In some implementations, the penile prosthesis implantation device is used to dilate the corpora cavernosum.

DETAILED DESCRIPTION

Current instrumentation for penile prosthesis implantation could sometimes place the urethra at higher than necessary risk during passage of Keith needles through the glans penis. Multiple instruments may be required to accomplish safe passage of the Keith needles and the process is also dependent upon surgeons protecting the urethra manually. The disclosed penile prosthesis implantation apparatus and related methods address these shortcomings by dilating the corpora cavernosa and facilitating safer placement of the cylinders or the rods. The disclosed penile prosthesis implantation apparatus combines several steps into one step to avoid multiple instrument passages. The disclosure reduces chances of urethral injury by combining dilation and measuring of the corpora cavernosum into one step. This is accomplished by moving the urethra away from the tip of the dilator while the dilator is advanced distally in the corpora cavernosum. Once an appropriately sized prosthesis is selected, a diagonal channel running through the penile prosthesis implantation device is used to pass the Keith needles laterally, away from the urethra.

Figure 1:
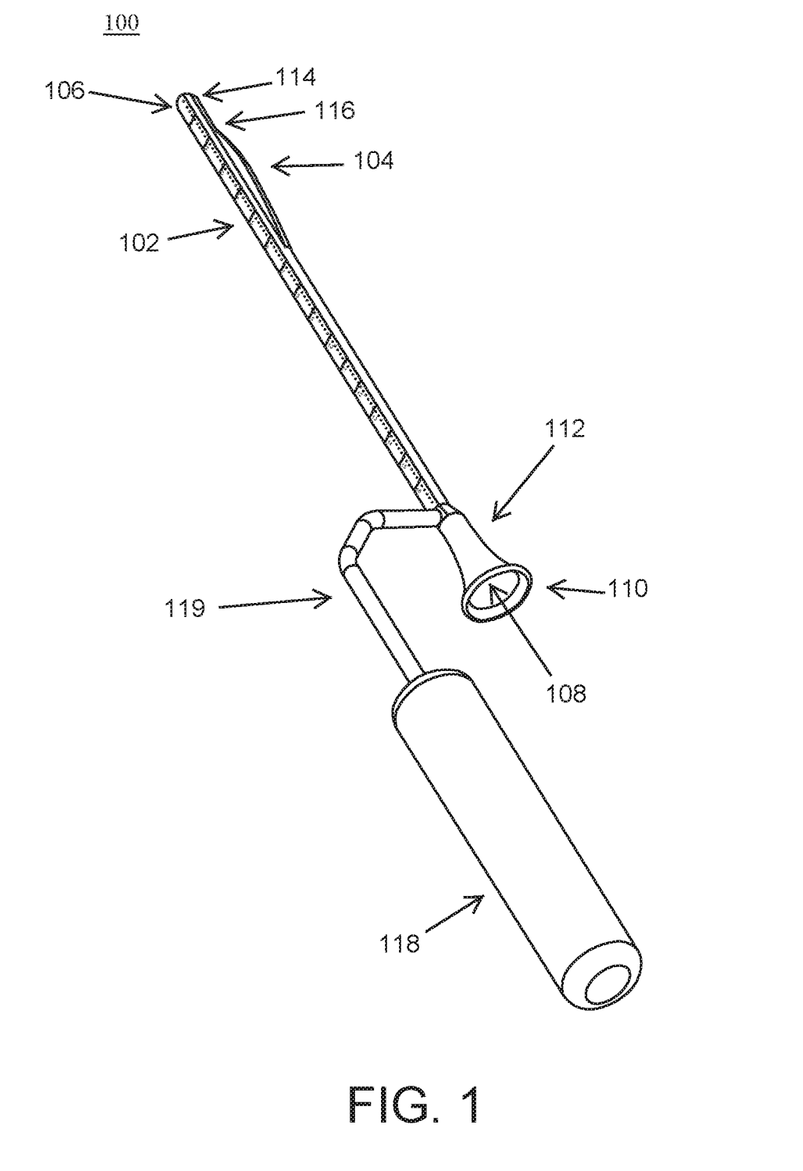
FIG. 1 is a diagram showing a top view of an example penile prosthesis implantation device in accordance with some implementations.

FIGS. 1-6 show diagrams of an example penile prosthesis implantation device (e.g., 100) and/or components thereof. In FIG. 1, a top view of the penile prosthesis implantation device 100 is shown in accordance with some implementations. The penile prosthesis implantation device 100 shown includes a rod 102 (e.g., a rounded-corner square rod) of a predetermined length and circumference. The rod 102 includes a crescendo/decrescendo "bump" or protrusion 104 of predetermined width situated on one side of the rod at a predetermined distance proximal to a distal tip 106. The rod includes a channel 108 of a predetermined diameter that is straight, but extends diagonally through the rod 102. The channel 108 can be accessed by a fluted entry 110 of predetermined width at the proximal end 112 of the rod 102.

The channel 108 extends diagonally through the rod 102 from the side with the bump 104 proximally to the side opposite the bump 104 distally. The distal end 114 near the distal tip 106 has a slot 116 of predetermined width on one side to facilitate the loading of a Keith needle and attached prosthesis suture into the distal end 114, the slot meets and opens into the distal end of the channel 108, a bottom of the slot also opens into the channel 108. An offset handle 118 begins from the proximal end 112 of the rod 102 on the side opposite the bump 104. The handle 118 is connected to the rod 102 by an offset connection member 119. A needle pusher 120 (see FIG. 6) that is separate is used to push the Keith needle out of the distal end 114 of the device. On one end of the needle pusher 120, a flat syringe-style plunger 122 is placed for a user to push the Keith needle through.

Figure 2:
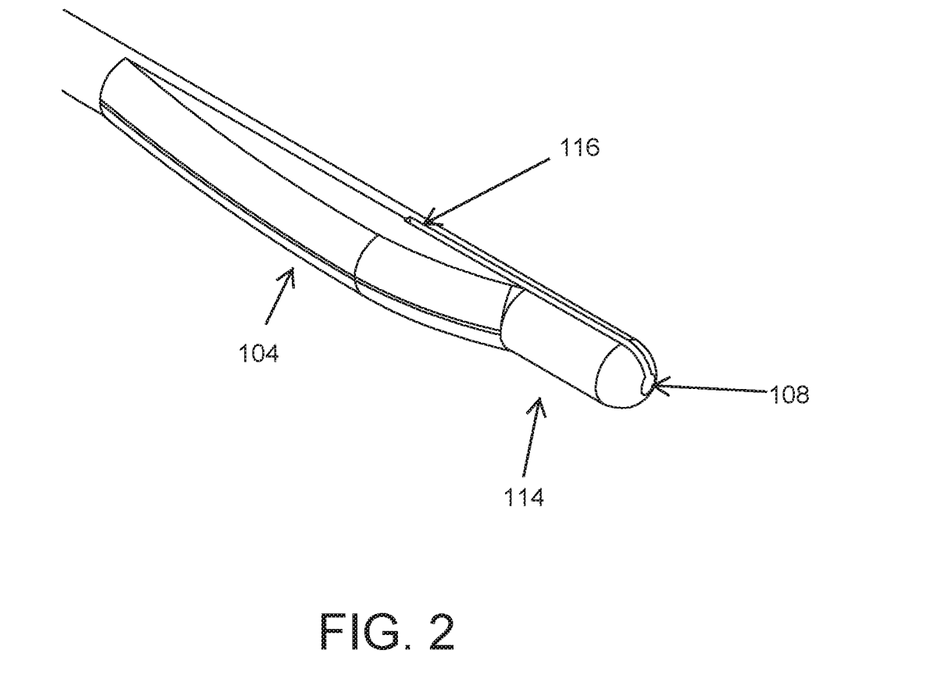
FIG. 2 is a diagram showing a top view of a distal end of an example penile prosthesis implantation device in accordance with some implementations.

FIG. 2 shows a top view of a distal end of an example penile prosthesis implantation device 100 in accordance with some implementations. The penile prosthesis implantation device shown in this view includes details of the distal end 114 such as the protrusion 104, the slot 116 for loading the Keith needle and suture, and the distal opening 108.

Figure 3:
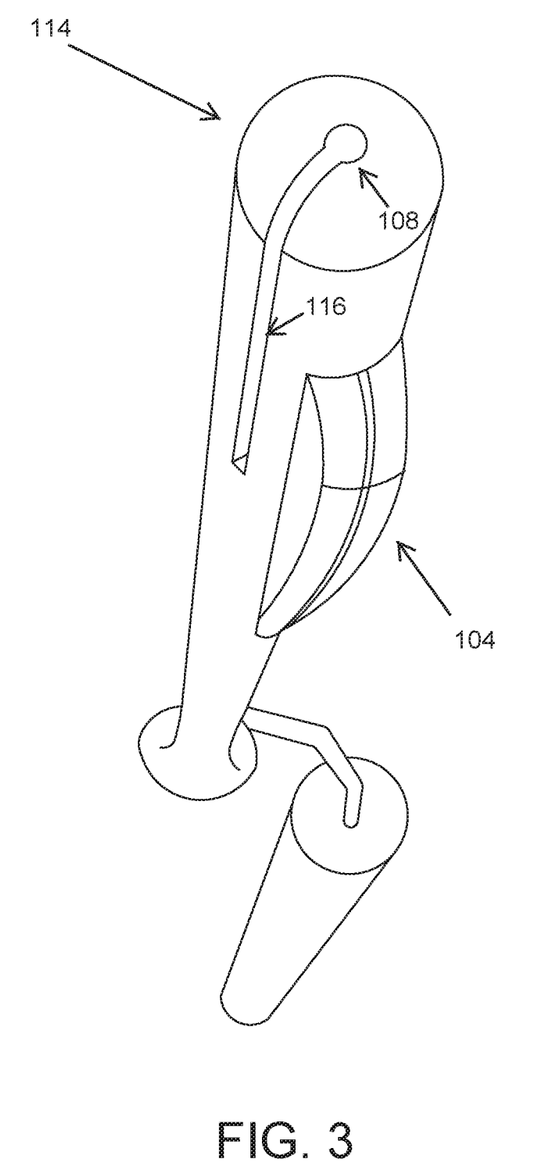
FIG. 3 is a diagram showing a perspective view of a distal end of an example penile prosthesis implantation device in accordance with some implementations.

FIG. 3 is a diagram showing a perspective view of a distal end 114 of an example penile prosthesis implantation device in accordance with some implementations. The penile prosthesis implantation device shown in this view includes details of the distal end 114 such as the protrusion 104, the slot 116 for loading the Keith needle and suture, and the distal opening 108.

Figure 4:
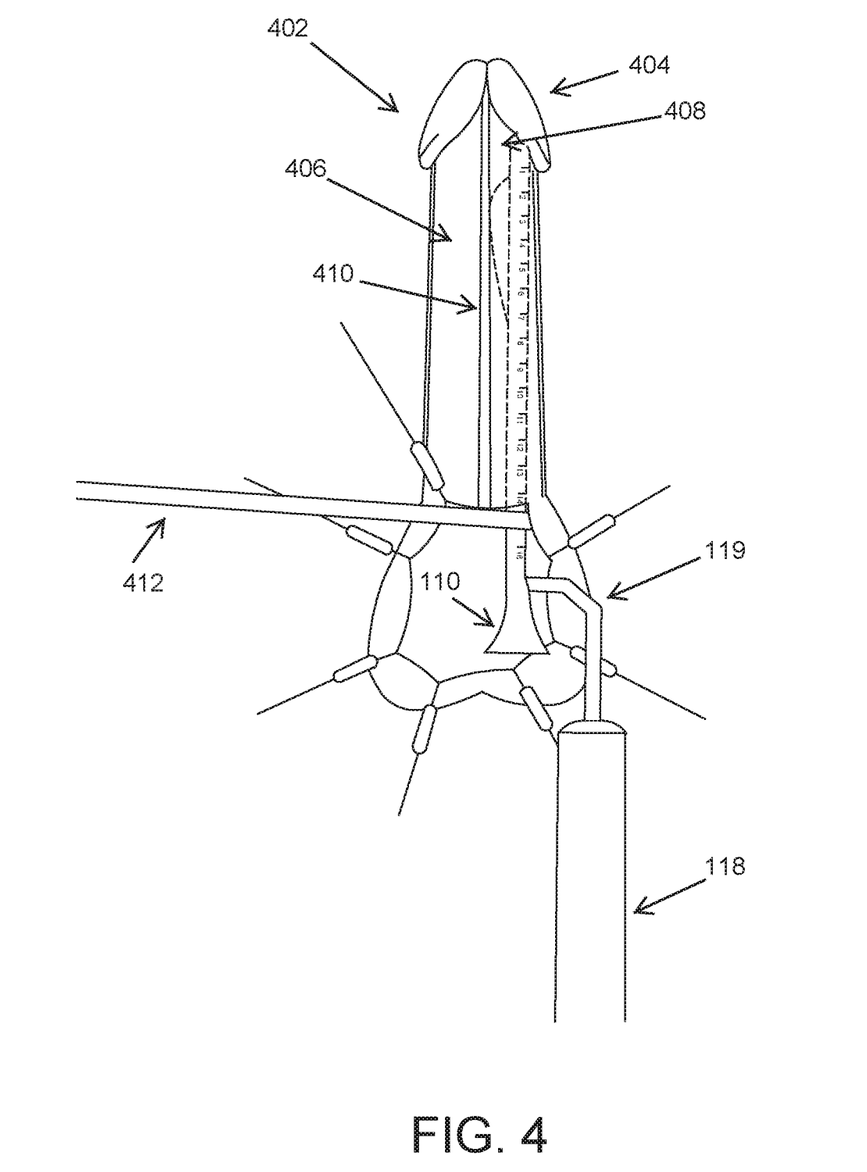
FIG. 4 is a diagram showing an example penile prosthesis implantation device in use for distal measurement in accordance with some implementations.

FIG. 4 is a diagram showing an example penile prosthesis implantation device in use for distal measurement in accordance with some implementations. FIG. 4 shows a diagram of a penis 402 that includes features shown such as the glans penis 404, corpora cavernosum 406 and 408, and urethra 410. FIG. 4 also shows penile prosthesis sutures 412.

Figure 5:
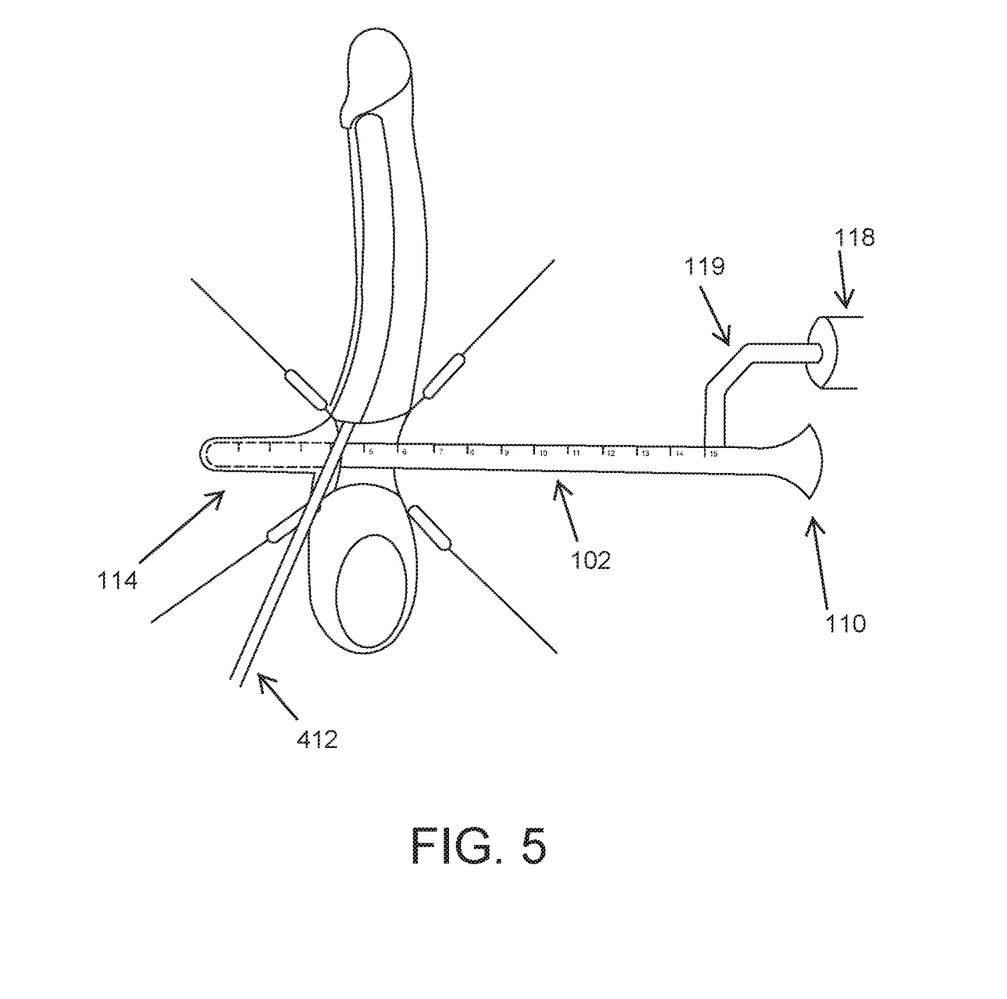
FIG. 5 is a diagram showing an example penile prosthesis implantation device in use for proximal measurement in accordance with some implementations.

FIG. 5 is a diagram showing an example penile prosthesis implantation device in use for proximal measurement in accordance with some implementations.

FIGS. 4 and 5 show an example process/method for measuring the length of corpora cavernosum can include opening the corpora cavernosum via corporotomy and advancing a penile prosthesis implantation device distally through the corpora cavernosum 408 to measure a distal corporal length, wherein an offset handle of the penile prosthesis implantation device is directed laterally away from a penis. The method can further include, as shown in FIG. 5, withdrawing the penile prosthesis implantation device from the corpora cavernosum and advancing the penile prosthesis implantation device 102 proximally through the corpora cavernosum to measure a proximal corporal length of the corpora cavernosum also.

Figure 6:
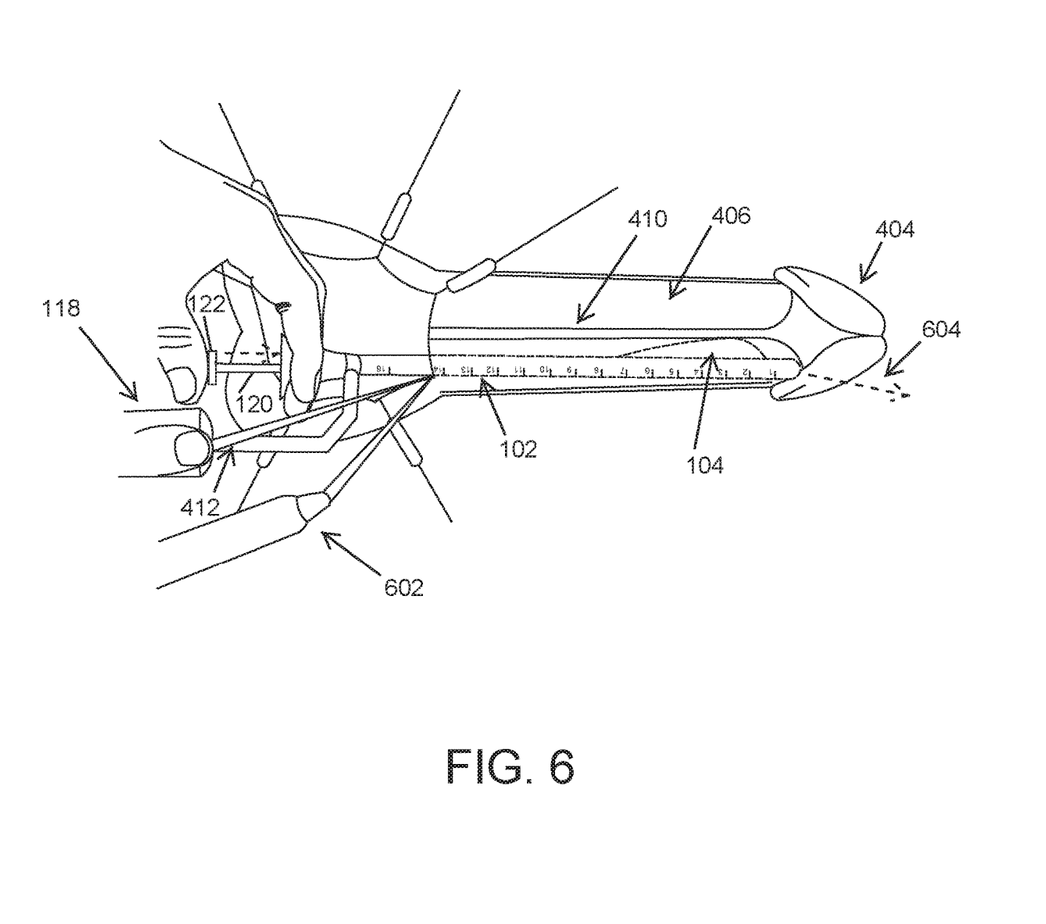
FIG. 6 is a diagram showing an example penile prosthesis implantation device in use for pushing a Keith needle in accordance with some implementations.

FIG. 6 shows the device 100 in use during an example process/method for implanting a penile prosthesis. The method can include opening the corpora cavernosum via corporotomy and selecting a prosthesis 602. The method can also include threading sutures 412 of the penile prosthesis through an eye of a Keith needle. The method can further include loading the Keith needle into a distal tip (e.g., into the slot) of a penile prosthesis implantation device 102. The method can also include bringing out the sutures through a distal slot of the penile prosthesis implantation device. The method can further include holding the sutures 412 in place against a handle of the penile prosthesis implantation device to prevent the Keith needle from protruding from the distal tip of the penile prosthesis implantation device. The method also includes advancing the penile prosthesis implantation device distally through the corpora cavernosum with the handle directed laterally away from a penis. The method further includes advancing a needle pusher through a fluted entrance of the penile prosthesis implantation device once the penile prosthesis implantation device is in glans penis until the Keith needle pierces the glans penis 404 and advances along a path 604 away from the urethra 410.

The penile prosthesis implantation device and/or one or more of its components can be made of materials such as metal, plastics, and/or other natural or synthetic materials. In some implementations, the rod, the offset handle, and the needle pusher with flat syringe-style plunger can each form a single integrated unit without one or more joints, attachments, or connections.

The penile prosthesis implantation device can be used to address erectile dysfunctions in some implementations. It will be appreciated that the penile prosthesis implantation apparatus described herein is for illustration purposes only and is not intended to be limiting. Other penile prosthesis implantation apparatus may be used depending on a contemplated implementation. It will be appreciated that the penile prosthesis implantation device components described herein are for illustration purposes only and are not intended to be limiting. Other types, shapes, sizes, and materials of the components may be used depending on a contemplated implementation.

In some implementations, dimensions of an example penile prosthesis implantation device can include a 20-centimeter plastic or metal rounded-corner square/rectangular rod of 1.5-centimeter circumference with a 3-centimeter crescendo/decrescendo "bump" or protrusion situated on one side of the rod 1.5-centimeter proximal to the distal tip. The rod also includes a straight channel of 2-millimeter diameter, which channel is accessed by a 2-centimeter fluted entry at the proximal end of the rod. The channel extends diagonally through the rod from the side with bump proximally to the side opposite the bump distally. The distal end has a 3-centimeter slot on one side to facilitate loading a Keith needle and attached prosthesis suture into the distal end. An offset handle extends off the proximal end of the rod on the side opposite the bump. A separate 24-centimeter long 1.7-millimeter diameter needle pusher is used to push the Keith needle out of the distal end of the device. One end of the needle pusher includes a flat syringe-style plunger for a user to use to push the Keith needle through. It will be appreciated that any dimensions described herein are for illustration purposes only and are not intended to be limiting. Other dimensions could be used depending on a contemplated implementation.

It is therefore apparent that there are provided, in accordance with the various example implementations disclosed herein, a penile prosthesis implantation apparatus and related methods.

While the disclosed subject matter has been described in conjunction with a number of implementations, it is evident that many alternatives, modifications and variations would be or are apparent to those of ordinary skill in the applicable arts. Accordingly, Applicants intend to embrace all such alternatives, modifications, equivalents and variations that are within the spirit and scope of the disclosed subject matter.

What is claimed is:

1. A penile prosthesis implantation device comprising:
a rod having a protrusion disposed on a first side of the rod at a distance proximal to a distal end of the rod;
a channel inside the rod accessed by a fluted entry at a proximal end of the rod, the channel extending diagonally though the rod and exiting at a channel opening at the distal end of the rod;
a slot formed at the distal end of the rod and opening into the channel opening at a distal end of the slot, wherein a bottom of the slot opens into the channel;
an offset handle extending from the proximal end of the rod on a second side of the rod; and
a needle pusher having a flat syringe-style plunger at a proximate end.

2. The penile prosthesis implantation device of claim 1, wherein the slot is configured to accept loading of one or more of a Keith needle or a prosthesis suture.

3. The penile prosthesis implantation device of claim 1, wherein the channel extends diagonally through the rod from the first side of the rod proximally to the second side of the rod opposite the first side distally.

4. The penile prosthesis implantation device of claim 1, wherein the needle pusher is operable to push a Keith needle out of the distal end of the rod.

5. The penile prosthesis implantation device of claim 1, wherein the flat syringe-style plunger is operable to push a Keith needle through the channel.

6. The penile prosthesis implantation device of claim 1, wherein the penile prosthesis implantation device is operable to dilate corpora cavernosum.

7. The penile prosthesis implantation device of claim 1, wherein the penile prosthesis implantation device is operable to measure a proximal length of a corpora cavernosum.

8. The penile prosthesis implantation device of claim 1, wherein the penile prosthesis implantation device is operable to distally measure a corpora cavernosum.

9. A method for implanting a penile prosthesis, the method comprising:
opening corpora cavernosum via corporotomy;
selecting the penile prosthesis;
threading sutures of the penile prosthesis through a Keith needle;
loading the Keith needle into a distal tip of a penile prosthesis implantation device;
bringing out the sutures through a distal slot of the penile prosthesis implantation device;
holding the sutures in place against an offset handle of the penile prosthesis implantation device;
preventing the Keith needle from protruding from the distal tip of the penile prosthesis implantation device;
advancing the penile prosthesis implantation device distally through a corpora cavernosum with the offset handle directed laterally away from a penis; and
advancing a needle pusher through a fluted entrance of the penile prosthesis implantation device, once the penile prosthesis implantation device is in place, causing the Keith needle to pierce and exit from the glans penis.

10. The method of claim 9, wherein the Keith needle exits the glans penis at an angle which situates the exit of the Keith needle away from the urethra.

11. The method of claim 9, wherein the distal tip has a slit to facilitate loading of the Keith needle.

12. The method of claim 9, wherein the distal tip has a slit to facilitate loading of a prosthesis suture.

13. The method of claim 9, wherein the sutures are passed through a channel of the penile prosthesis implantation device.

14. The method of claim 13, wherein the channel extends diagonally through the penile prosthesis implantation device from a first side of the penile prosthesis implantation device proximally to a second side of the penile prosthesis implantation device opposite the first side distally.

15. The method of claim 9, wherein the needle pusher pushes the Keith needle out of the distal tip of the penile prosthesis implantation device, and wherein the handle is directed laterally.

16. The method of claim 9, wherein the handle extends from a proximal end of the penile prosthesis implantation device.

17. The method of claim 9, wherein a flat syringe-style plunger is placed on one end of the needle pusher to push the Keith needle through the penile prosthesis implantation device.

18. A method for measuring length of corpora cavernosum, the method comprising:
opening the corpora cavernosum via corporotomy;
advancing a penile prosthesis implantation device distally through the corpora cavernosum to measure a distal corporal length, wherein an offset handle of the penile prosthesis implantation device is directed laterally away from a penis;
withdrawing the penile prosthesis implantation device from the corpora cavernosum; and
advancing the penile prosthesis implantation device proximally through the corpora cavernosum to measure a proximal corporal length of the corpora cavernosum.

19. The method of claim 18, wherein the offset handle extends from a proximal end of the penile prosthesis implantation device.

20. The method of claim 18, wherein the penile prosthesis implantation device is used to dilate the corpora cavernosum.

* * * * *